United States Patent
Choi et al.

(10) Patent No.: US 8,154,206 B2
(45) Date of Patent: Apr. 10, 2012

(54) PORTABLE MICROWAVE PLASMA GENERATOR CAPABLE OF GENERATING PLASMA WITH LOW ELECTRIC POWER

(75) Inventors: Jun Choi, Pohang-si (KR); Felipe Iza, Leicestershire (GB); Jae Koo Lee, Pohang-si (KR)

(73) Assignees: Postech Foundation, Pohang-Si (KR); Postech Academy Industry Foundation, Pohang-Si (KR)

( * ) Notice: Subject to any disclaimer, the term of this patent is extended or adjusted under 35 U.S.C. 154(b) by 447 days.

(21) Appl. No.: 12/365,534

(22) Filed: Feb. 4, 2009

(65) Prior Publication Data
US 2010/0052539 A1    Mar. 4, 2010

(30) Foreign Application Priority Data
Aug. 26, 2008    (KR) .................. 10-2008-0083364

(51) Int. Cl.
H05B 31/26    (2006.01)
H05H 1/30    (2006.01)

(52) U.S. Cl. ............. 315/39.3; 315/111.21; 315/111.01; 315/111.11; 219/121.48

(58) Field of Classification Search .................. 606/33, 606/34, 39, 40, 41, 45; 315/39.3, 111.21–111.91; 219/121.48; 422/186.04
See application file for complete search history.

(56) References Cited

U.S. PATENT DOCUMENTS

| | | | | |
|---|---|---|---|---|
| 7,102,345 | B2 * | 9/2006 | Jackson | 324/72.5 |
| 7,795,818 | B2 * | 9/2010 | Urayama et al. | 315/111.21 |
| 7,858,899 | B2 * | 12/2010 | Fujii et al. | 219/121.48 |
| 2002/0022836 | A1 * | 2/2002 | Goble et al. | 606/34 |
| 2002/0101162 | A1 * | 8/2002 | Ikeda et al. | 315/39.3 |
| 2004/0027113 | A1 * | 2/2004 | Jackson | 324/72.5 |
| 2007/0210038 | A1 * | 9/2007 | Fujii et al. | 219/121.48 |
| 2010/0074808 | A1 * | 3/2010 | Lee | 422/186.04 |
| 2010/0327155 | A1 * | 12/2010 | Lopez-Avila et al. | 250/282 |

FOREIGN PATENT DOCUMENTS

| | | |
|---|---|---|
| CN | 1954647 A | 4/2007 |
| JP | 06-188094 A | 7/1994 |
| JP | 2006-104545 A | 4/2006 |
| JP | 2006-202662 A | 8/2006 |

* cited by examiner

*Primary Examiner* — Vibol Tan
(74) *Attorney, Agent, or Firm* — Kile Park Goekjian Reed & McManus PLLC

(57) ABSTRACT

There is provided a small-sized portable microwave plasma generator capable of generating plasma at atmospheric pressure with low electric power including a coaxial cable, an outer conductor, a connection conductor, and a connection member. The coaxial cable includes a first inner conductor and a dielectric material encircling the first inner conductor. The outer conductor encircles the coaxial cable. The connection conductor includes at least one gas inlet tube. The connection conductor electrically connects between the first inner conductor and the outer conductor at one end of the coaxial cable. The connection member includes a second inner conductor passing through the outer conductor and then connecting to the first inner conductor.

8 Claims, 5 Drawing Sheets

[FIG. 1]
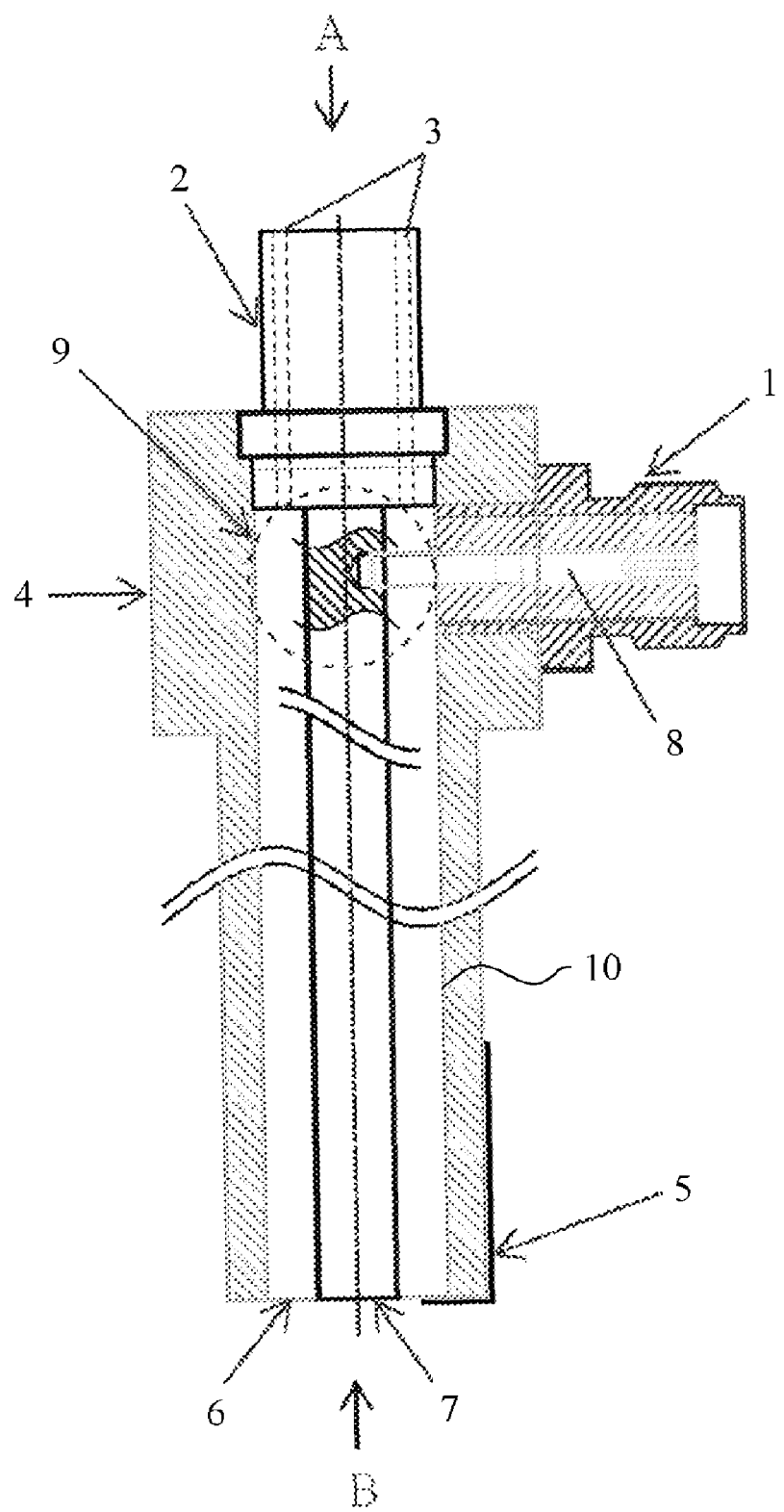

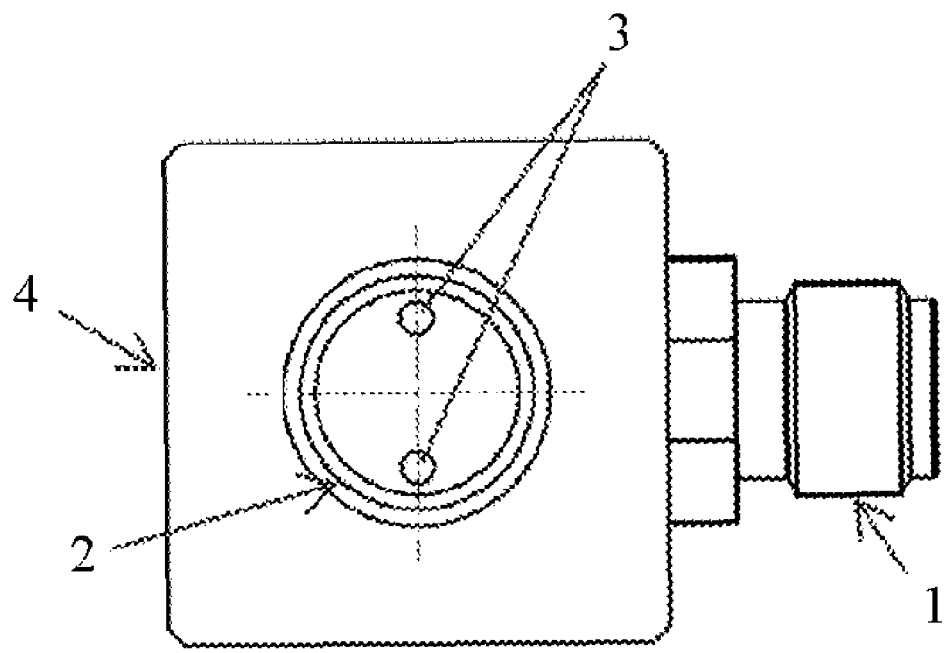
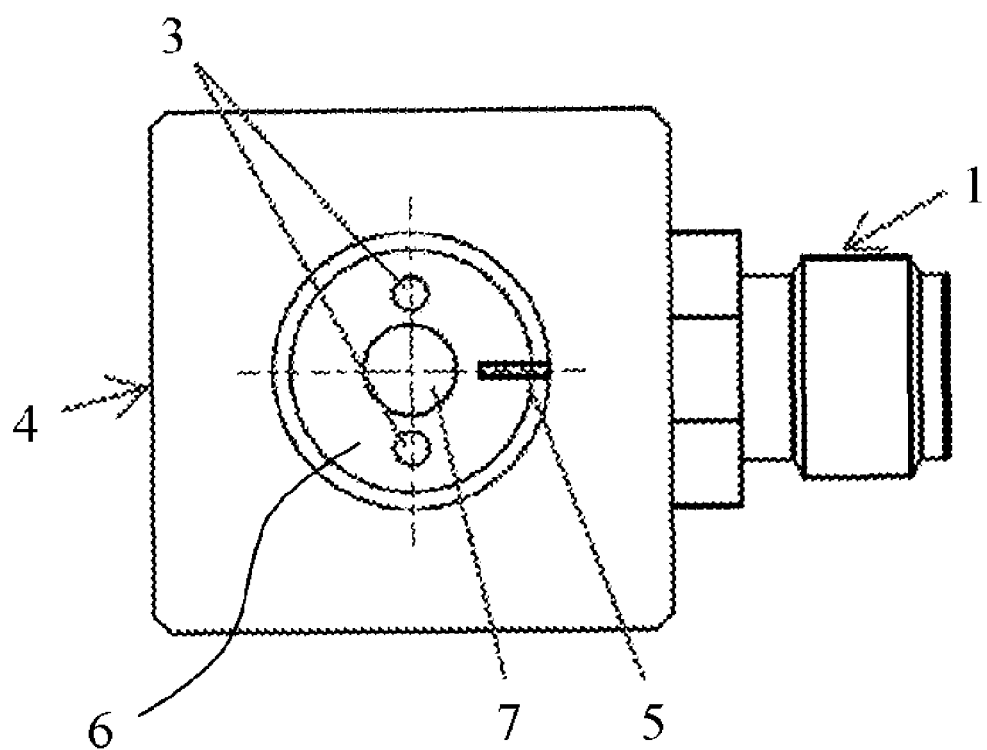

[FIG. 4]
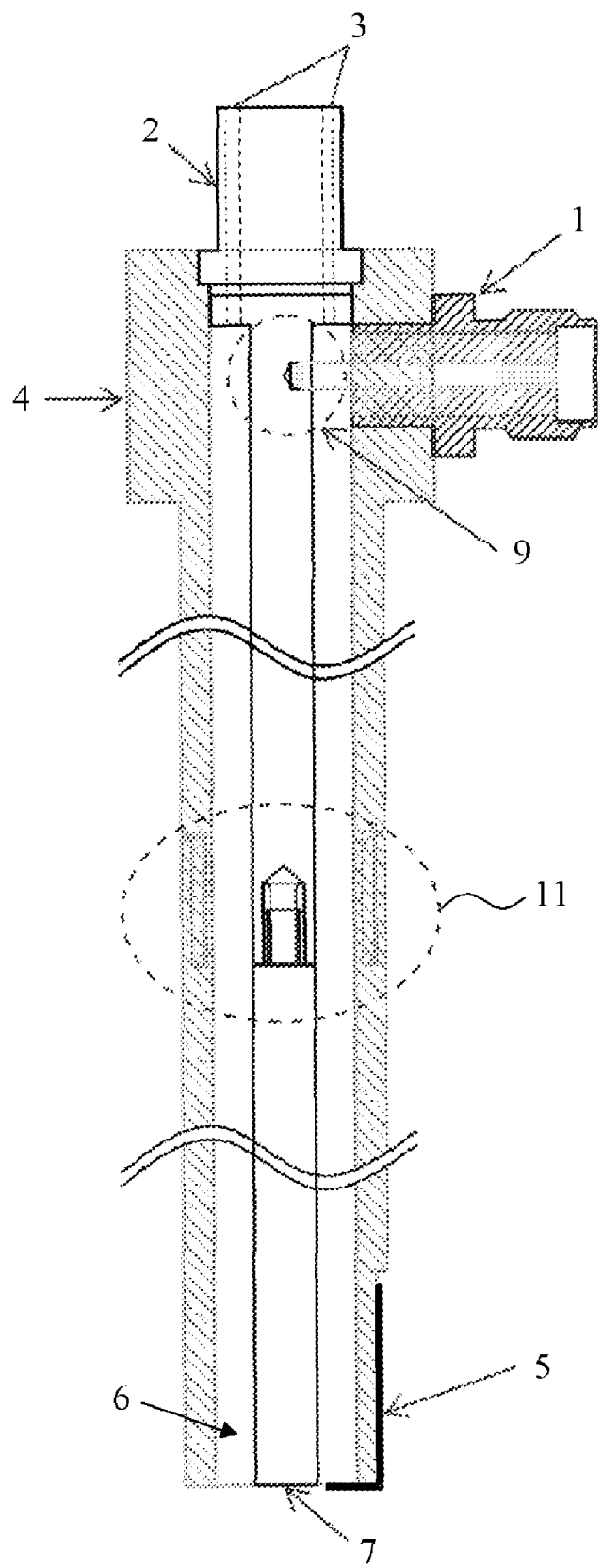

[FIG. 7]
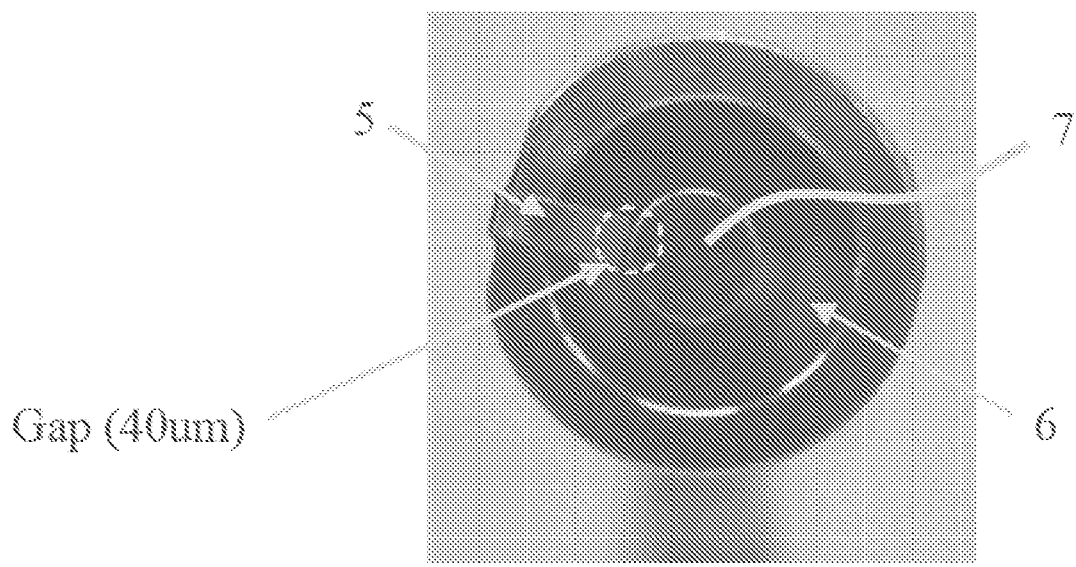
Gap (40um)
[FIG. 8]
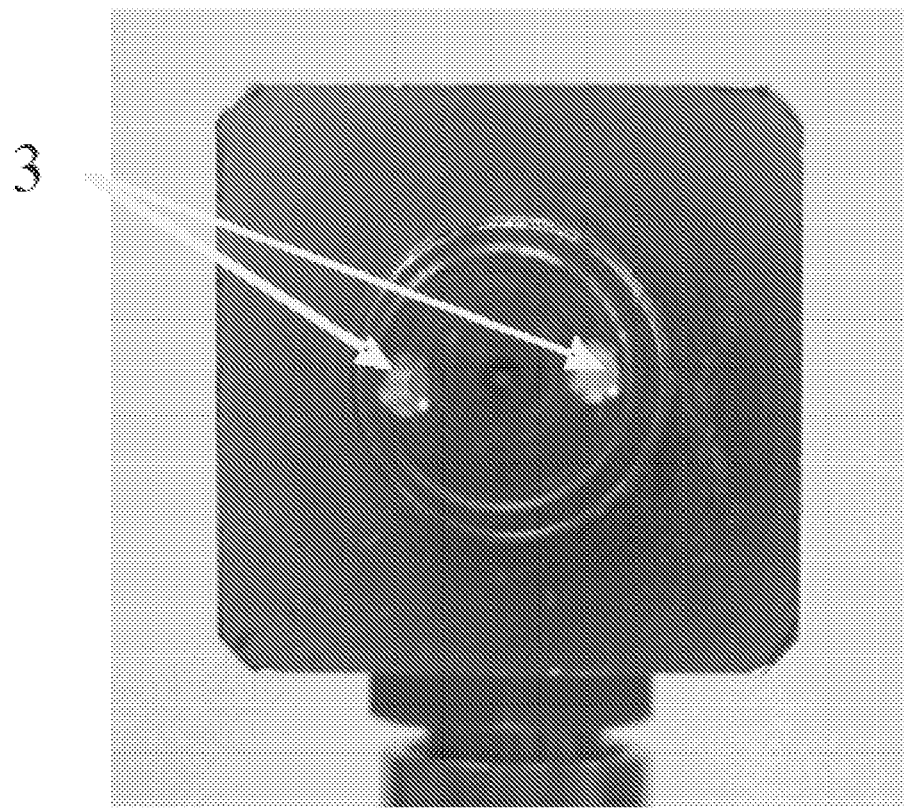

PORTABLE MICROWAVE PLASMA GENERATOR CAPABLE OF GENERATING PLASMA WITH LOW ELECTRIC POWER

BACKGROUND OF THE INVENTION

1. Field of the Invention

The present invention relates to a plasma generator, and more particularly to a small-sized microwave plasma generator capable of generating plasma with low electric power.

2. Description of the Background Art

A plasma torch is a device that generates a directed flow of plasma from its nozzle. The plasma jet can be used to melt a solid, or evaporate a solid or a liquid, or heat a gas to increase enthalpy in a closed thermodynamic system under constant and entropy.

A conventional microwave plasma generator, usually equipped with a magnetron, consumes more than 100 watts to operate. A conventional microwave plasma generator, equipped with a rectangular waveguide, is too bulky to carry. A coaxial microwave plasma torch, equipped with an antenna-shaped discharge tube may substitute for the conventional microwave plasma generator, but is also too large-sized to carry.

The conventional microwave plasma generator is currently in use which generates plasma at atmospheric pressure, using various types of electric power sources. A great deal of research has gone into developing a microwave plasma generator which generates plasma without thermal effect with low electric power by using a microwave with a frequency of 900 Mega Hertz or 2.45 Giga Hertz.

Worldwide research has been done on application of plasma to the biomedical field. The U.S. FDA approved the use of the microwave plasma generator in medical treatment of wrinkles and speckles on the human skin. Development of a portable microwave plasma generator consuming less than 5 watts at atmospheric pressure will expand its application to cancer treatment, dental care, cosmetic treatment, disinfection, coagulation, sterilization, air purification, and so forth.

BRIEF DESCRIPTION OF THE INVENTION

Therefore, an object of the present invention is to provide a small-sized portable microwave plasma generator capable of generating plasma at atmospheric pressure with low electric power.

According to an aspect of the present invention, there is provided a portable microwave plasma generator capable of generating plasma with low electric power. Including a coaxial cable, an outer conductor, a connection conductor; and a connection member. The coaxial cable includes a first inner conductor and a dielectric material encircling the first inner conductor. The outer conductor encircles the coaxial cable. The connection conductor includes at least one gas inlet tube. The connection conductor electrically connects between the first inner conductor and the outer conductor at one end of the coaxial cable. The connection member includes a second inner conductor passing through the outer conductor and then connecting to the first inner conductor.

The portable microwave plasma generator is less than 10 cm in length and generates plasma at atmospheric pressure with low electric power. The portable microwave plasma generator is capable of matching its impedance with impedance of a microwave oscillator supplying a microwave without having to use a separate impedance matching device.

The foregoing and other object, feature, aspect and advantage of the present invention will become more apparent from the following detailed description of the present invention when taken in conjunction with the accompanying drawings.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 1 is a cross-sectional view of a portable microwave plasma generator capable of generating plasma with low electric power according to the present invention;

FIG. 2 is a front view of the A direction end of the portable microwave plasma generator capable of generating plasma with low electric power, as shown in FIG. 1;

FIG. 3 is a front view of the B direction end of the portable microwave plasma generator capable of generating plasma with low electric power, as shown in FIG. 1;

FIG. 4 is a view of the portable microwave plasma generator capable of generating plasma with low electric power, having the coaxial cable whose the length is adjustable;

FIG. 7 is a front view of the right end F of the portable microwave plasma generator capable of generating plasma with low electric power, as shown in FIG. 6; and FIG. 8 is a front view of the left end R of the portable microwave plasma generator capable of generating plasma with low electric power, as shown in FIG. 6.

DETAILED DESCRIPTION OF THE INVENTION

Figure 5:
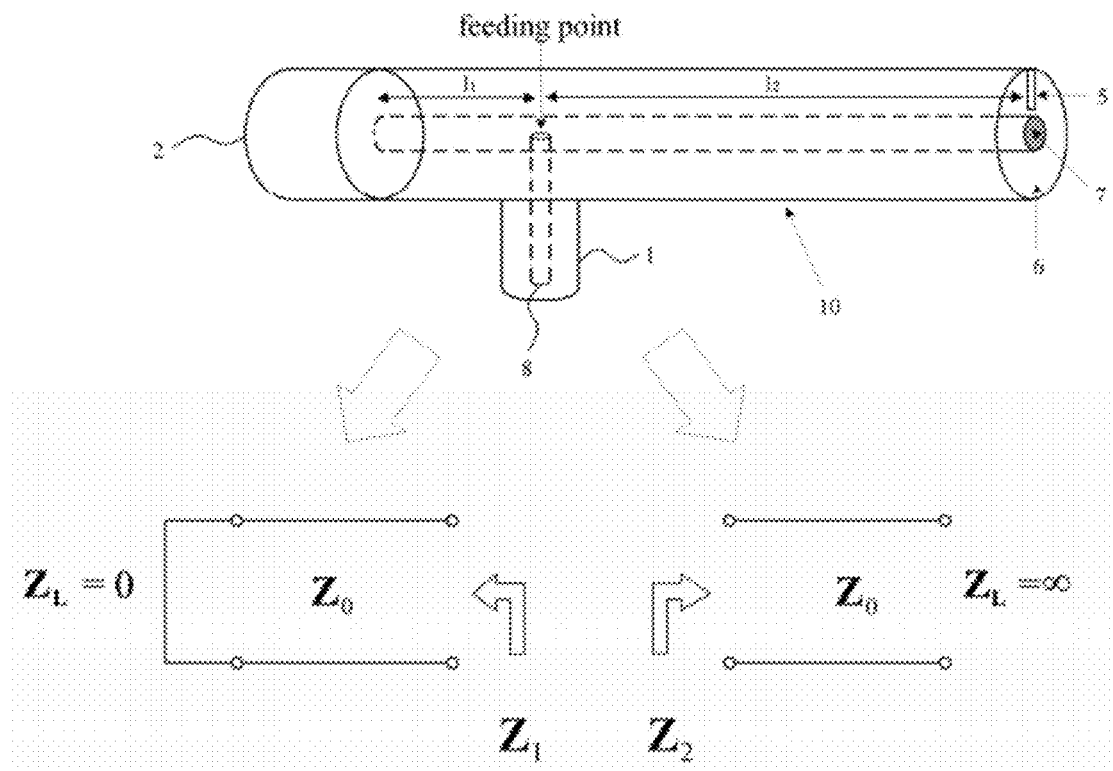
FIG. 5 is a schematic view of the portable microwave plasma generator capable of generating plasma with low electric power, according to the present invention.

Reference will now be made in detail to the preferred embodiment of the present invention, an example of which is illustrated in the accompanying drawings.

FIG. 1 is a cross-sectional view of a portable microwave plasma generator capable of generating plasma with low electric power according to the present invention.

As shown in FIG. 1, the portable microwave plasma generator 100 capable of generating plasma with low electric power includes a coaxial cable 10, an outer conductor 4, a connection conductor 2, a connection member 1, and a discharge tip 5.

The coaxial cable 10 includes a first inner conductor 7 and a dielectric material 6 encircling the first inner conductor 7. The outer conductor encircles the coaxial cable 10. The connection conductor 2 includes at least one gas inlet tube 3. The connection conductor 2 electrically connects between the first inner conductor 7 and the outer conductor 4 at one end of the coaxial cable 10. The connection member 1 includes a second inner conductor 8 passing through the outer conductor 4 and then electrically connects to the first inner conductor 7 at a feeding point 9. The connection member 1 is conductive. An insulating material may be provided between the second inner conductor 8 and the connection member 1. The discharge tip 5, provided on the other end of the coaxial cable 10, serves to minimize electric power consumption when generating plasma on the coaxial cable 10.

The portable microwave plasma generator 100 according to the present invention generates plasma using resonance energy of a microwave with a frequency of 900 Mega Hertz or 2.45 Giga Hertz which is applied through the second inner conductor 8. The connection member 1, the connection conductor 2, the outer conductor 4, the first inner conductor 7, and the second inner conductor 8 electrically connects to each other and function as a resonator oscillating the microwave. The microwave converts into a TEM (Transverse electromagnetic) wave on the coaxial cable 10. The TEM wave is a transverse wave, carrying electromagnetic energy, which has not an electric field component and a magnetic field component in the propagation direction, but has the electric field component and the magnetic field component in the direction perpendicular to the propagation direction.

Air is used as the dielectric material 6 between an outer jacket of the coaxial cable 10 and the first inner conductor 7. That is, the dielectric 6 is an empty space into which an inert gas is introduced to be ionized. The introduced gas becomes in a state of plasma by resonance energy of the microwave resonating and amplified on the conductors 2, 4, 7, and 8 to which the microwave is applied, and discharges toward the bottom of the portable microwave plasma generator, i.e., in the direction B. A fluorocarbon solid (PTFE such as Teflon) may be used as the dielectric material 6.

A length of the coaxial cable 10 may be ¼ (one-third) or ¾ (three-fourth) of a wavelength of the microwave which is suitable for the microwave to produce resonance. When the length of the coaxial cable 10 is set to this length, the electric field strength becomes maximized at the end of the resonator which is in the direction B, thereby generating plasma more easily.

Relation between a speed of light, a frequency and a length of the microwave is expressed as the following equation. 1.

$$\lambda = \frac{C}{f \cdot \sqrt{\varepsilon\gamma}}$$ [EQUATION 1]

where λ is a wavelength of the microwave, C is a speed of light, f is a frequency of the microwave, and ∈r is a relative dielectric constant. The relative dielectric constant is 1 (one) when the dielectric material is an air and is 2.1 when the dielectric material is a fluorocarbon solid (PTFE such as Teflon).

For example, the frequency of the microwave is 900 MHz, the length λ of the microwave is expressed as the following equation 2.

$$\lambda = \frac{3 \cdot 10^8}{900 \cdot 10^6} = 0.333[m] = 33.3[cm]$$ [EQUATION 2]

According to the equation 2, ¼ (one-fourth) of the microwave is approximately 8.33 cm. This makes it possible to manufacture the portable microwave plasma generator which is around 10 cm in length.

An input impedance of the coaxial cable 10 seen from the feeding point 9 where the first inner conductor 7 of the coaxial 10 and the second inner conductor 8 of the connection member 1 come in contact with each other varies depending upon a position of the feeding point 9. By adjusting the position of the feeding point 9, the impedance matching can easily be made between a microwave oscillator (not shown) applying the microwave to the coaxial cable 10 through the second inner conductor 8 and the microwave plasma generator or between an amplifier amplifying the microwave outputting from the microwave oscillator and the microwave plasma generator. This is later described in more detail.

Generation of plasma at atmospheric pressure requires high electric field strength of $10^6$ V/m (Volts/meter) or more. The discharge tip 5 is used to locally increase the electric field strength. The discharge tip 5 does not need to be used, after discharge occurs and plasma is generated. The discharge tip 5, when not in use, may be removed from the microwave plasma generator. Experimental findings show that the portable microwave plasma generator according to the present invention generates plasma with about 1 watt or so.

FIG. 2 is a front view of the A direction end of the portable microwave plasma generator capable of generating plasma with low electric power, as shown in FIG. 1.

As shown in FIG. 2, the connection conductor 2 is inserted into the middle of the outer conductor 4. And the two gas inlet tubes 3, through which the inert gas is introduced into the dielectric material 6, are provided to the connection conductor 2. The single inlet tube 3 may be provided to the connection conductor 2. The inert gas includes helium and argon.

FIG. 3 is a front view of the B direction end of the portable microwave plasma generator capable of generating plasma with low electric power, as shown in FIG. 1.

As shown in FIG. 3, the outer conductor 4 encircles the coaxial cable 10 which has the first inner conductor 7 at the center, and the dielectric material 6 is provided between the outer jacket of the coaxial cable 10 and the first inner conductor 7. The discharge tip 5 is positioned on the end of the coaxial cable 10, which is in the direction B. The discharge tip 5 discharges plasma outputting in the direction B.

FIG. 4 is a view of the portable microwave plasma generator capable of generating plasma with low electric power, having the coaxial cable whose the length is adjustable.

As shown in FIG. 4, a coaxial cable extension tab 11, oval-shaped part (marked dotted line) in the middle of the portable microwave plasma generator 400 serves to adjust the length of the outer conductor 4 of the coaxial cable and the length of the first inner conductor 7 of the coaxial cable. For example, the outer conductor 4 of the coaxial cable 10 and the first inner conductor 7 of the coaxial cable 10 may be expandable or contractable in a slidable manner or in an attachable and detachable manner to adjust the length of the coaxial cable 10.

Adjustment of the length of the coaxial cable 10 with the coaxial cable extension tab 11 makes it possible not only to effectively produce resonance, but also to make the impedance matching which prevents the microwave from being reflected. The lower part of the coaxial cable 10 and the upper part of the coaxial part including the extension tab 11 may attach to or detach from each other. This makes it possible to replace of the coaxial cable 10 including the extension tab 11, when the end of the resonator is eroded away by plasma, thereby extending the life of the microwave plasma generator.

The portable microwave plasma generator capable of generating plasma with low electric power according to the present invention can adjust its impedance by adjusting the position of the connection member 1. This removes the need of installing the impedance match device to make the impedance matching between the microwave oscillator (not shown) applying the microwave to the coaxial cable 10 through the second inner conductor 8 and the microwave plasma generator or between an amplifier amplifying the microwave outputting from the microwave oscillator and the microwave plasma generator.

Operation of the portable microwave plasma generator and relation between it and its peripheral devices are now described.

FIG. 5 is a schematic view of the portable microwave plasma generator capable of generating plasma with low electric power, according to the present invention.

Referring to FIG. 5, the input impedance $Z_{IN}$ of the coaxial cable 10 seen from the feeding point 9 where the first inner conductor 7 of the coaxial cable 10 and the second inner conductor 8 of the connection member 1 come in contact with each other is expressed as the following equation 3.

$$Z_{IN} = Z_1 \| Z_2 = Z_0 \left[ \frac{1}{\tanh(jkl_1)} + \tanh(jkl_2) \right]^{-1} \quad \text{[EQUATION 3]}$$

$$\approx Z_0 \left[ \left( \frac{\alpha l_1}{\sin^2(\beta l_1)} + \frac{\alpha l_2}{\cos^2(\beta l_2)} \right) + j(-\cot(\beta l_1) + \tan(\beta l_2)) \right]$$

Where a first impedance $Z_1$ is an impedance of the coaxial cable 10 to the left of the feeding point 9, a second impedance $Z_2$ is an impedance of the coaxial cable to the right of the feeding point 9, $Z_0$ is a characteristic impedance of the coaxial cable 10, j is a complex number $\sqrt{-1}$, $I_1$ is a distance between the feeding point 9 and the left end of the coaxial cable 10, $I_2$ is a distance between the feeding point 9 and the right end of the coaxial cable 10, k is a complex propagation constant or a wave number which is a reciprocal number of wavelength, $\alpha$ is an attenuation constant of the coaxial cable 10, and $\beta$ is a phase constant of the coaxial cable 10. The equation 3 is written on the assumption that when ($\alpha$ l)=1(one), tan($\alpha$ l)≈($\alpha$ l).

The left end of the coaxial cable 10 connects to the connection conductor 2, so a load impedance $Z_L$ of the first impedance $Z_1$ is 0 (zero). The right end of the coaxial cable 10 opens, so the load impedance is ∞ (infinite). The attenuation constant $\alpha$ of the coaxial cable 10, and the phase constant $\beta$ of the coaxial cable 10 are constants which are automatically determined by the electric characteristics of the coaxial cable 10. So, the input impedance $Z_{IN}$ i.e., the input impedance $Z_{IN}$ of the resonator is determined by $I_1$ and $I_2$.

When the length of the coaxial cable 10 is less than ¼ (one-fourth) of the wavelength of the microwave, adjustment of $I_1$ means adjustment of inductance of the resonator, and adjustment of $I_2$ means adjustment of capacitance of the resonator. So, the resonator corresponds to what consists of the resistor, the inductor, and the capacitor which connect in parallel to each other. Thus, the position of the feeding point 9 is determined by adjusting any one of $I_1$ and $I_2$. When the input impedance $Z_{IN}$ is set to 50Ω(Ohm), the separate impedance matching device does not need to be installed.

This is about the coaxial cable 10 of which the length is ¼ (one-fourth) or ¾ (three-fourth) of the wavelength of the microwave. This may be applied to the coaxial cable 10 of which the length is any one of multiples of ¼ (one-fourth) and multiples of ¾ (three-fourth) of the wavelength of the microwave.

Figure 6:
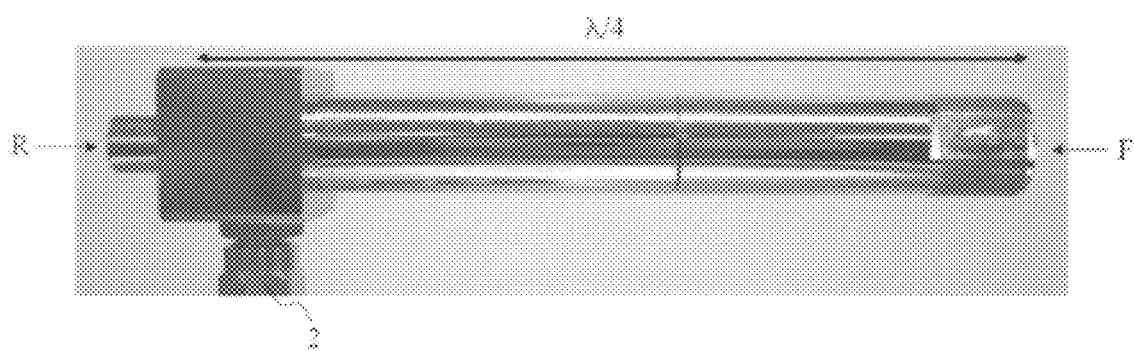
FIG. 6 is a picture of an actual product embodying the portable microwave plasma generator capable of generating plasma with low electric power, according to the present invention.

FIG. 6 is a picture of an actual product embodying the portable microwave plasma generator capable of generating plasma with low electric power, according to the present invention.

As show in FIG. 6, the length of the coaxial cable 10 in the portable microwave plasma generator is ¼ (one-fourth) of wavelength of the microwave. A SMA (Sub Miniature version A) connector is used as the connection member 1.

FIG. 7 is a front view of the right end F of the portable microwave plasma generator capable of generating plasma with low electric power, as shown in FIG. 6.

As shown in FIG. 7, there is a given gab between the discharge tip 5 and the first inner conductor 7 at the right end of the portable microwave plasma generator. If the portable microwave plasma generator makes resonance using the microwave with a frequency of 900 MHz and the length of the coaxial cable 10 is ¼ (one-fourth) of the wavelength of the microwave, then the gap is 40 μm (micro meter). If the portable microwave plasma generator makes resonance using the microwave with a frequency of 2.45 GHz and the length of the coaxial cable 10 is ¾ (three-fourth) of the wavelength of the microwave, then the gap is 100 μm.

FIG. 8 is a front view of the left end R of the portable microwave plasma generator capable of generating plasma with low electric power, as shown in FIG. 6.

As shown in FIG. 8, the inert gas is introduced into the gas inlet tube 3.

As above described, the coaxial cable 100 designed for the specific purpose is employed in the portable microwave plasma generator according to the present invention. However, a general type of the semi rigid coaxial cable in wide use may be instead employed. The voltage and the electromagnetic field become at a maximum at the end of the resonator, i.e., at the end of the portable microwave plasma generator. As a result, the portable microwave plasma generator according to the present invention effectively generates plasma, using electric power at a minimum, compared with the conventional microwave plasma generator. Furthermore, the length of the portable microwave plasma generator is made to be 10 cm or so that corresponds to one-fourth of the wavelength of the microwave. This makes portable the portable microwave plasma generator. The portable microwave plasma generator does not require the installation of separate impedance matching device, if the impedance of the resonator is adjusted to 50Ω, the output impedance of the microwave oscillator.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalents of such metes and bounds are therefore intended to be embraced by the appended claims.

What is claimed is:

1. A portable microwave plasma generator capable of generating plasma with low electric power comprising:
   a coaxial cable comprising:
      a first inner conductor; and
      a dielectric material encircling the first inner conductor;
   an outer conductor encircling the coaxial cable;
   a connection conductor, comprising at least one gas inlet tube, electrically connecting between the first inner conductor and the outer conductor at one end of the coaxial cable; and
   a connection member comprising a second inner conductor passing through the outer conductor and then connecting to the first inner conductor,
   wherein the dielectric material is air, an empty space into which to introduce an inert gas, and a microwave is applied through the second inner conductor,
   wherein the inert gas is one selected from a group consisting of helium and argon, and
   wherein a point where the microwave is applied is adjusted by adjusting a position of the connection member, thereby making impedance matching of the portable microwave plasma generator.

2. The portable microwave plasma generator capable of generating plasma with low electric power, according to claim 1, wherein the microwave has a frequency of 900 MHz or 2.45 GHz.

3. The portable microwave plasma generator capable of generating plasma with low electric power, according to claim 1, wherein a length of the coaxial cable is ¼ (one-fourth), or ¾ (three-fourth) of a wavelength of the microwave.

4. The portable microwave plasma generator capable of generating plasma with low electric power, according to claim 1, wherein a length of the coaxial cable is any one of multiples of ¼ (one-fourth) and multiples of ¾ (three-fourth) of a wavelength of the microwave.

5. The portable microwave plasma generator capable of generating plasma with low electric power, according to claim 1, wherein the coaxial cable comprises at least two parts which are attachable to and detachable from each other or are slidable into each other in a manner that adjust the length of the coaxial cable.

6. The portable microwave plasma generator capable of generating plasma with low electric power, according to claim 2, further comprising a discharge tip, provided on the other end of the coaxial cable, discharging plasma on the coaxial cable.

7. The portable microwave plasma generator capable of generating plasma with low electric power, according to claim 6, wherein a gap between the discharge tip and the first inner conductor is 40 μm (micro meter) when the microwave has a frequency of 900 MHz.

8. The portable microwave plasma generator capable of generating plasma with low electric power, according to claim 6, wherein a gap between the discharge tip and the first inner conductor is 100 μm (micro meter) when the microwave has a frequency of 2.45 GHz.

* * * * *